US00PP34162P2

(12) United States Plant Patent
NeSmith

(10) Patent No.: US PP34,162 P2
(45) Date of Patent: Apr. 26, 2022

(54) RABBITEYE BLUEBERRY PLANT NAMED 'TO-3097'

(50) Latin Name: *Vaccinium virgatum*
Varietal Denomination: TO-3097

(71) Applicant: University of Georgia Research Foundation, Inc., Athens, GA (US)

(72) Inventor: D. Scott NeSmith, Griffin, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/476,108

(22) Filed: Sep. 15, 2021

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

*Primary Examiner* — Susan McCormick Ewoldt
(74) *Attorney, Agent, or Firm* — Thomas Horstemeyer, LLP

(57) ABSTRACT

A new and distinct cultivar of *Vaccinium* plant named 'TO-3097', characterized by a combination of unique pink-colored fruit, mid-season flowering and ripening, large berries with good firmness and flavor, high quality fruit production in conventional production areas, and a chilling requirement of about 450-500 hours below about 45° F.

6 Drawing Sheets

Botanical designation: *Vaccinium virgatum.*
Cultivar denomination 'TO-3097'.

BACKGROUND OF THE INVENTION

The present invention relates to a new and distinct cultivar of rabbiteye blueberry plant, botanically know as *Vaccinium virgatum*, and hereinafter referred to by the cultivar name 'TO-3097'.

The new *Vaccinium virgatum* 'TO-3097' was first identified in 2016 in Griffin, Ga. The new pink-fruited variety 'TO-3097' is mid-season, has large berries with unique pink color and good flavor and firmness, with no observed notable diseases or other pest problems beyond those also common for other varieties, and a chilling requirement of about 450-500 hours below about 45° F.

'TO-3097' is a product of a cross of 'T-459' (non-patented breeding selection) X 'T-743' (another non-patented breeding selection) made by D. Scott NeSmith in 2014. The new blueberry plant variety 'TO-3097' has been tested in asexually propagated (by vegetative cuttings) plantings in Alapaha, Ga. since 2018 where it was established for testing and comparing to industry standards. Observations of the resulting 'TO-3097' progeny have shown that the unique features of this new *Vaccinium virgatum* 'TO-3097' are stable and reproduced true to type in successive generations.

SUMMARY OF THE INVENTION

The new *Vaccinium* cultivar 'TO-3097' has not been observed under all possible environmental conditions. The phenotype may vary somewhat with variations in environment and cultural practices such as temperature, water and fertility levels, soil types, and light intensity without, however, any variance in genotype.

The following traits have been repeatedly observed and are determined to be the unique and distinguishing characteristics of the new *Vaccinium virgatum* cultivar named 'TO-3097'. In combination, these traits set 'TO-3097' apart from all other existing varieties of rabbiteye blueberry known to the inventors.

1. unique pink fruit color in various shades of pink, from wine-colored to lavender
2. large fruit with good flavor
3. mid-season for flowering and ripening in mid chill production regions
3. no significant diseases or pests not also common to other rabbiteye varieties.
4. high quality fruit production in conventional production areas with supplemental irrigation Comparison: As compared to the female parent 'T-459' and male parent 'T-743', plants of the new *Vaccinium* cultivar 'TO-3097' have a chilling requirement of about 450-500 hours, which is intermediate to 'T-459' (500 to 600 hours) and 'T-743' (300 to 400 hours). Both parents have typical medium to light blue fruit when mature, whereas, 'TO-3097' has the atypical pink hued, wine-colored fruit described earlier. 'TO-3097' flowers and ripens some 5 to 7 days later than 'T-743' and 5 to 7 days earlier than 'T-459'. Berry size of 'TO-3097' is similar to both parents.

Plants of the new *Vaccinium virgatum* can also be compared to other early season rabbiteye blueberry cultivars 'T-1101' Krewer™ (U.S. Plant Pat. No. 28,623) and 'T-959' Titan™ (U.S. Plant Pat. No. 24,135). The selection 'TO-3097' is mid-season and begins flowering around the same time as 'T-1101' Krewer™ but before 'T-959' Titan™ in South Georgia. It ripens near the time of 'T-959' Titan™ and after 'T-1101' Krewer™. 'TO-3097' has large berries, but smaller than both 'T-959' Titan™ and 'T-1101' Krewer™. 'TO-3097' has very good flavor and firmness (Table 1). Fruit color is very different than the medium to light blue fruit typical for Rabbiteye blueberries, including both 'T-959' Titan™ and 'T-1101' Krewer™. Instead, 'TO-3097' develops a mature fruit color that is various shades of pink, wine-colored, and lavender (see drawings). No notable diseases or other pest problems have been observed for the new variety that are not also common for other varieties. The new variety is estimated to have a chilling requirement of 450-500 hours, more or less, below 45° F. (based on comparison of flowering dates with those of known standard cultivars) when produced under typical mid chill production regions. Studies suggest that 'TO-3097' produces high quality fruit when grown in conventional production areas. Additional comparison data of 'TO-3097' with 'T-959' Titan™ and 'T-1101' Krewer™ are presented in the table below.

TABLE 1

Plant and fruit ratings for 'TO-3097' and standards grown in Alapaha, GA. Data represents and average of data from 2 years (2019, and 2020).

| | 'T-959' (Titan ™) | 'T-1101' (Krewer ™) | 'TO-3097' |
|---|---|---|---|
| Berry size | 8.8 | 8.5 | 7.8 |
| Berry scar | 7.2 | 7.5 | 7.5 |
| Berry firmness | 7.8 | 7.5 | 7.5 |
| Berry flavor | 7.2 | 7.2 | 7.5 |
| Cropping | 3.5 | 6.0 | 6.0 |
| Plant vigor | 9.0 | 8.5 | 8.5 |
| Date of 50% flowering | March 14 | March 5 | March 6 |
| Date of 50% ripening | June 3 | May 24 | June 1 |
| Fruit development period (days) | 81 | 80 | 87 |

BRIEF DESCRIPTION OF THE DRAWINGS

The accompanying colored photographic illustrations show the overall appearance and distinct characteristics of the new cultivar of *Vaccinium virgatum* 'TO-3097' showing the colors as true as possible. Colors in the photographs may differ slightly from the color values cited in the detailed botanical description, which accurately describes the colors of the new *Vaccinium virgatum* 'TO-3097'. The photographs were taken of plants grown outdoors in Alapaha, Ga. taken in March to July, 2020.

The photograph labeled

The photograph labeled

The photograph labeled

The photograph labeled

The photographs labeled

The photograph labeled

DETAILED BOTANICAL DESCRIPTION

Figure 1:
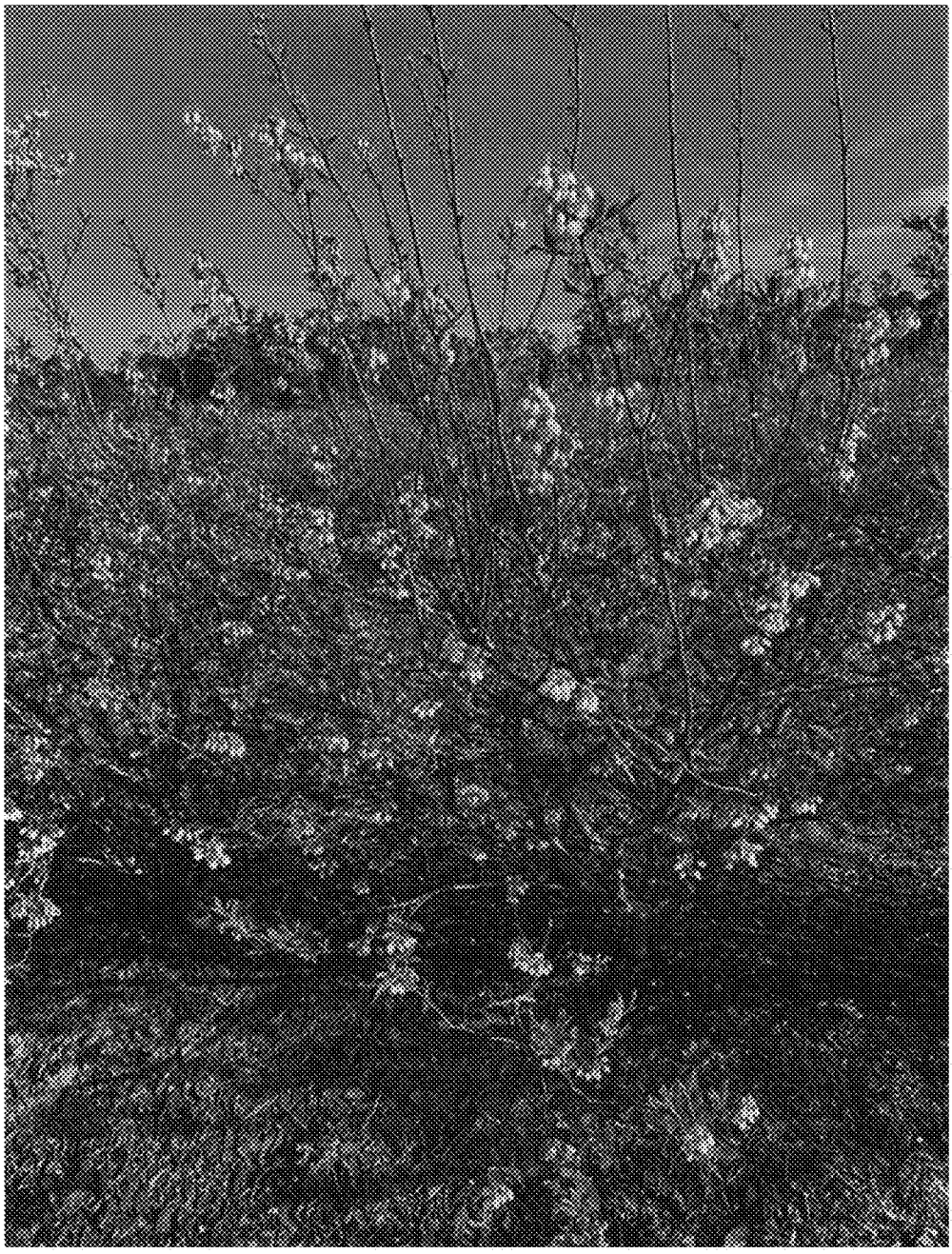
FIG. 1 depicts typical three-year old 'TO-3097' plants during flowering, taken in March.
Figure 2:
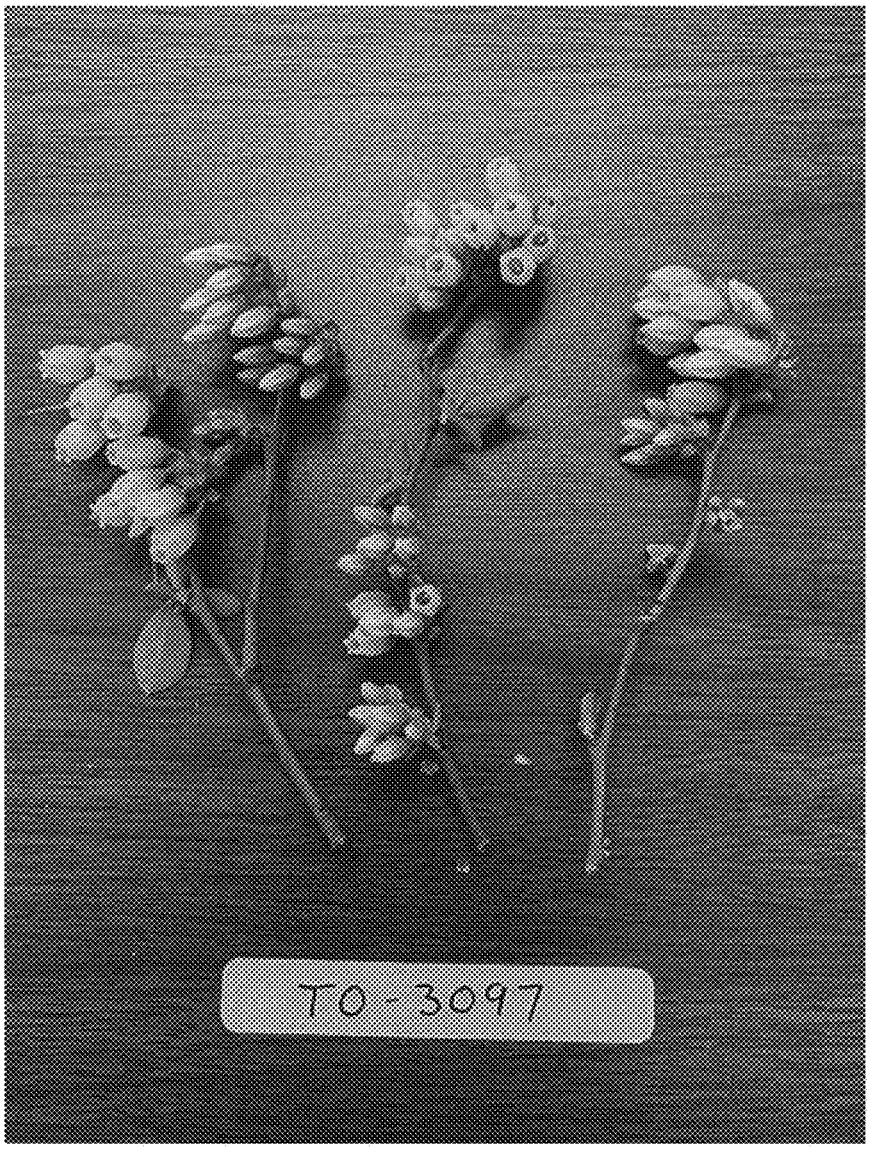
FIG. 2 depicts a close-up view of a flowering branch of a 'TO-3097' plant.
Figure 3:
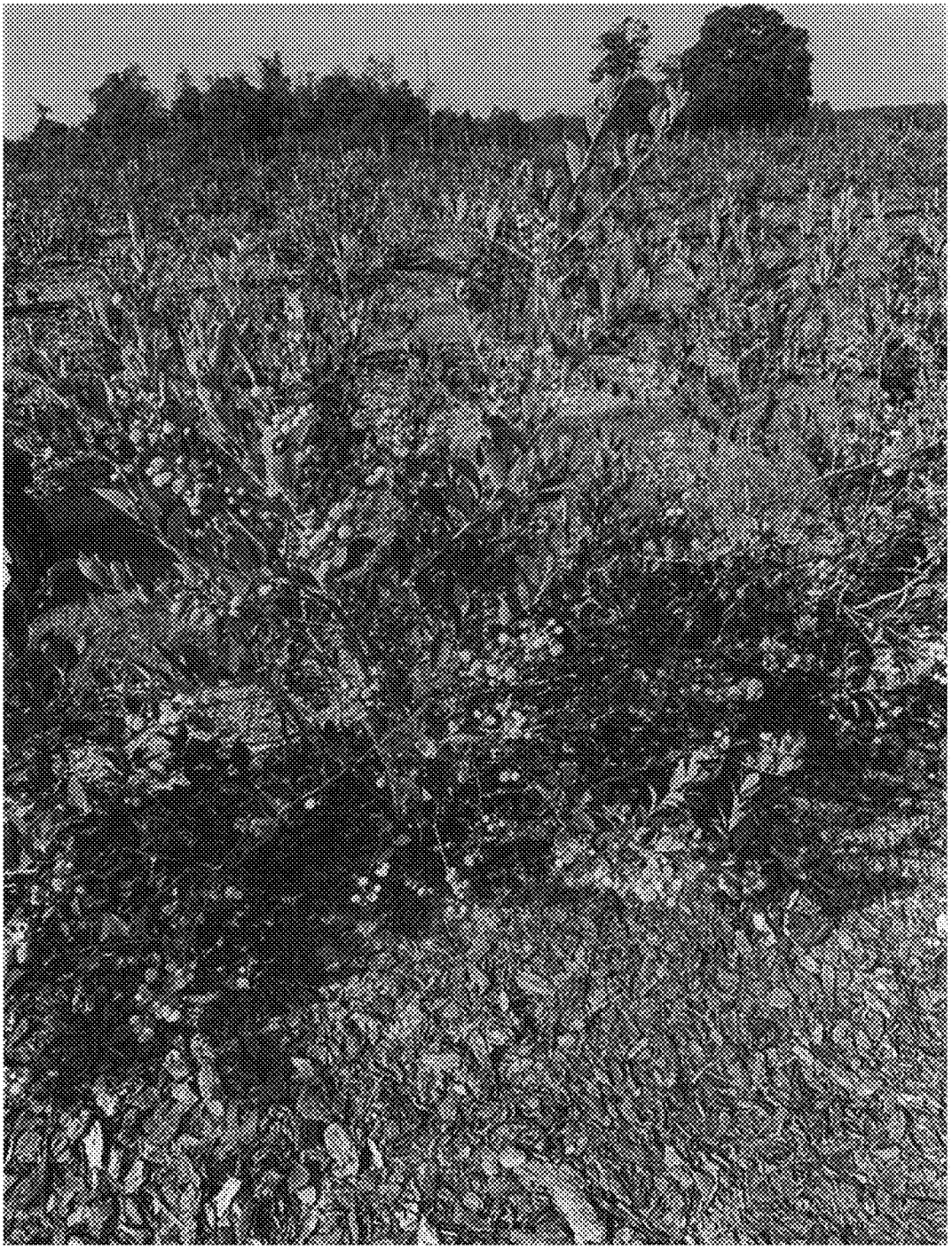
FIG. 3 depicts typical two-year old plants of 'TO-3097' during fruit ripening, taken in late May.
Figure 4:
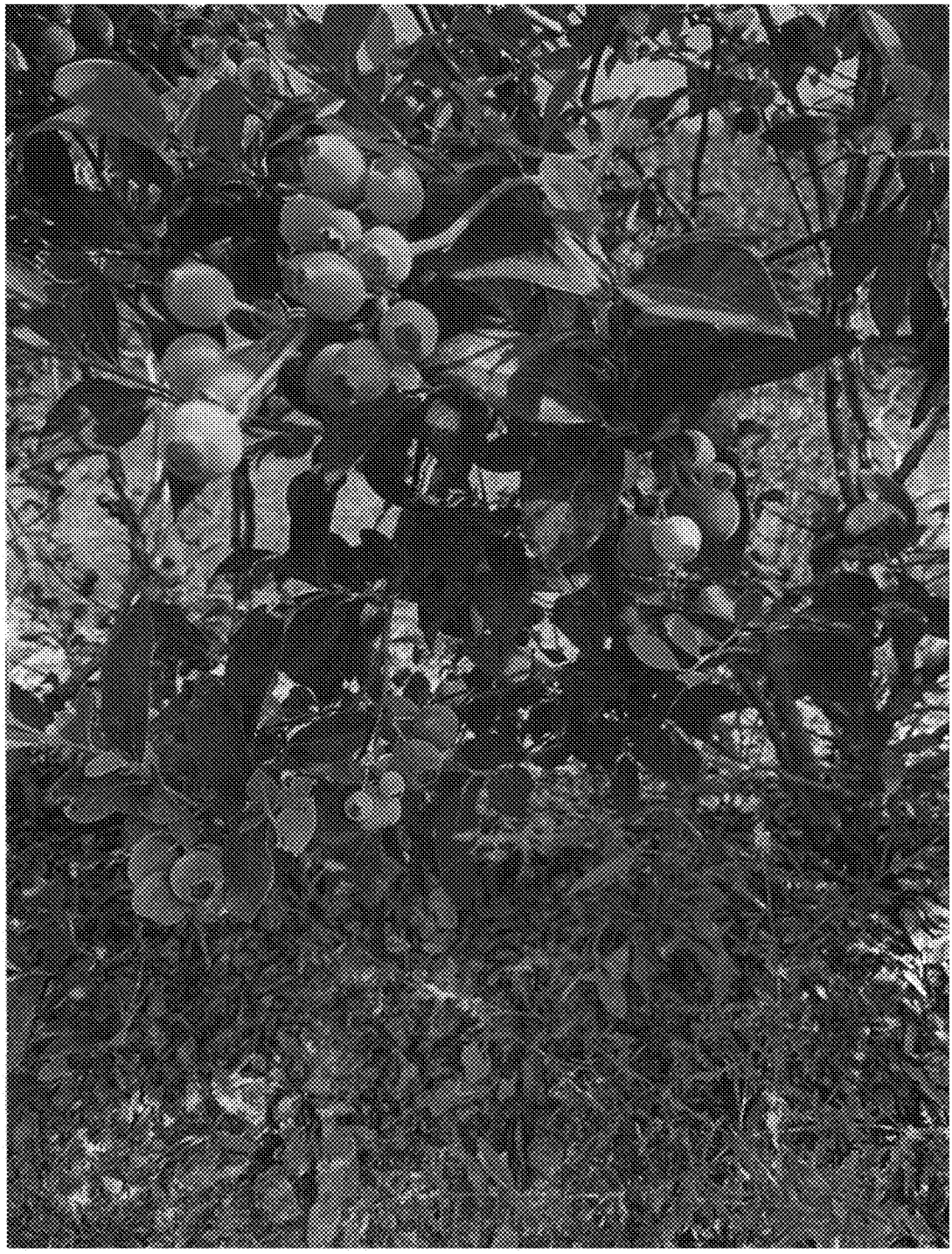
FIG. 4 depicts close-up view of maturing fruit (along with immature fruit) of 'TO-3097', taken in May.
Figure 5A:
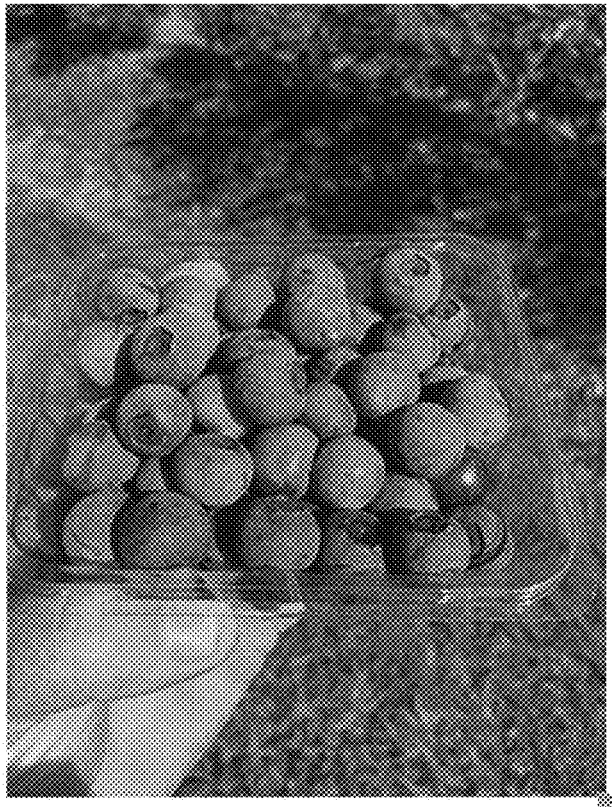
FIG. 5A and FIG. 5B are close-up views of ripe fruit of 'TO-3097', with FIG. 5A showing a container of ripe berries with the unique pink coloring and FIG. 5B depicting three sliced berries to reveal the inside of the fruit.
Figure 5B:
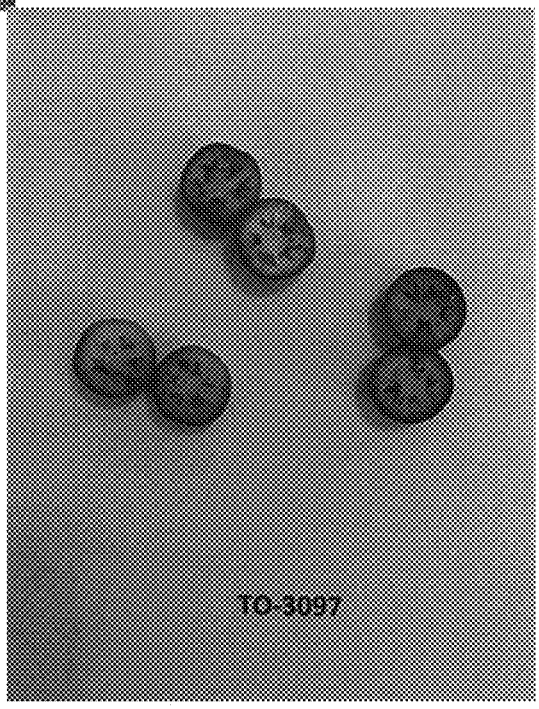
Figure 6:
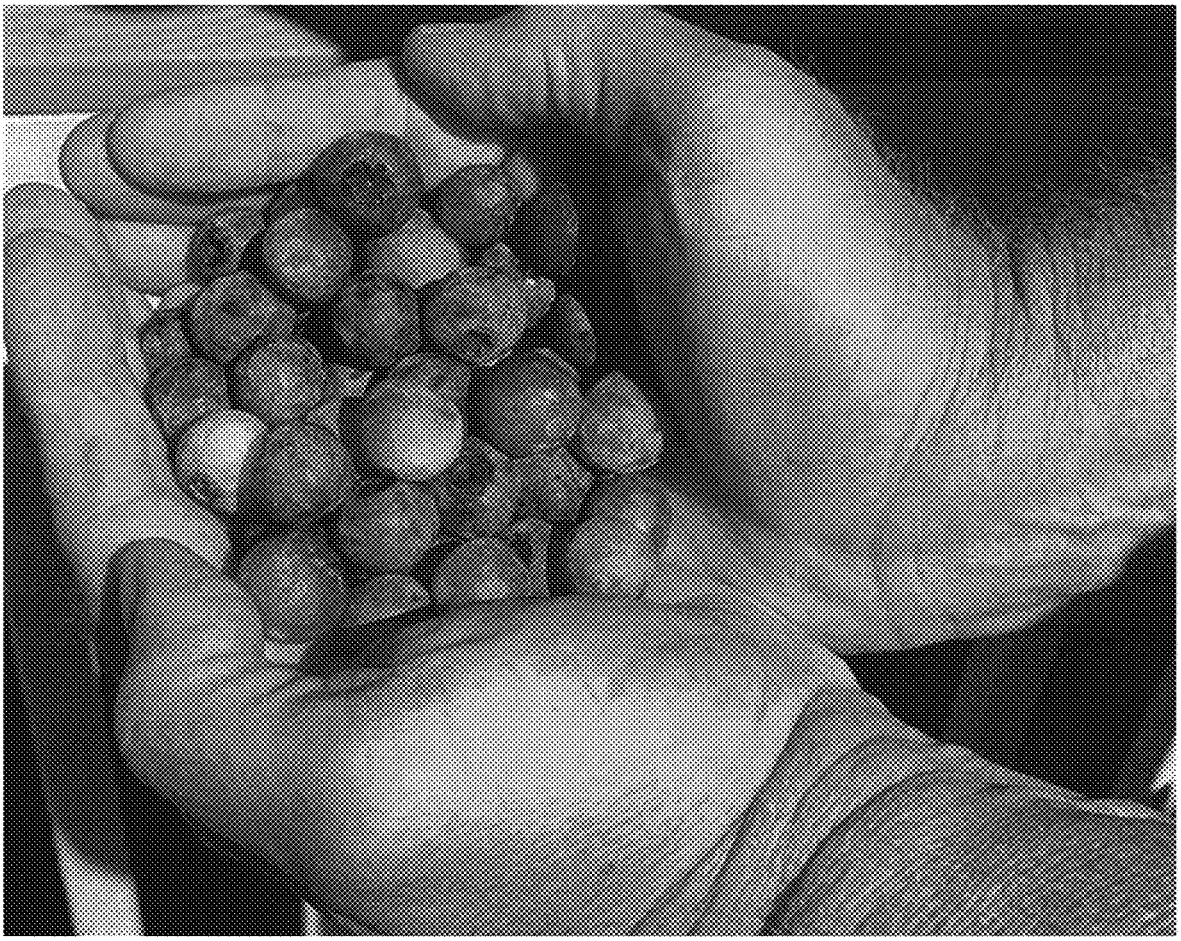
FIG. 6 is another close-up view of ripe fruit of 'TO-3097', in human hands, illustrating the pink coloring and relative size of the fruit.

The following traits have been consistently observed in the original plant of this new variety and in asexually propagated progeny grown in Alapaha, Ga., and, to the best knowledge of the inventors, their combination forms the unique characteristics of the new variety *Vaccinium virgatum* 'TO-3097'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2007, except where general terms of ordinary dictionary significance are used.

The aforementioned photographs and following observations, measurements, and values describe plants of the *Vaccinium virgatum* cultivar named 'TO-3097'. Data were collected between the years of 2019-2020 from a horticulture farm and nursery in Alapaha, Ga. from 3 to 4-year-old plants (planted in the field with supplemental irrigation). The average low temperature for the year ranges from about 54° F. to 58° F., and the average high temperature for the year ranges from about 78° F. to 82° F.

Botanical classification: *Vaccinium virgatum* 'TO-3097'.

*Commercial Classification.*—Fruit-bearing shrub.

*Parentage.*—'T-459' (non-patented breeding selection) X 'T-743' (non-patented breeding selection).

Growth and propagation:

*Propagation type.*—Vegetative by softwood cuttings.

*Growth rate.*—Highly vigorous.

*Root description.*—Fibrous.

Plant description:

*Growth habit.*—Plant is semi-upright, with 1 to 3 main canes arising from the original crown, and multiple branching of shoots from those canes 10 to 20 cm above ground.

*Usage.*—Commercial and private fruit production.

*Productivity.*—Medium to high yielding. Yields of 5 to 10 lbs per plant each year on plants 4 years old or older grown under well fertilized and irrigated field conditions.

*Size of plant.*—Plant is about 1.5 to 2.0 m tall by 3 to 4 years. Plants grown under highly productive soil and fertility conditions may exceed about 2.0 m tall in 4 years. The plant crown, or base, is narrow, typically about 10 to 20 cm in diameter. Upper portion of plant canopy reaches about 1.5 to 1.8 m in diameter by 3 to 4 years.

*Cold hardiness.*—Similar to other rabbiteye blueberry varieties such as 'T-959' (U.S. Plant Pat. No. 24,135) Titan™ and 'T-1101' (U.S. Plant Pat. No. 28,623) Krewer™.

*Disease resistance.*—No notable disease resistance or susceptibility observed. Estimated to be similar to other early season rabbiteye such as 'T-959' (U.S. Plant Pat. No. 24,135) Titan™ and 'T-1101' (U.S. Plant Pat. No. 28,623) Krewer™.

*Chilling requirement.*—Plants are medium chill, requiring only 450 to 500 hours, more or less, of temperatures at or below 45° F. (7° C.) to induce normal leafing and flowering during the spring. The chill requirement is less than the female parent 'T-459' (non-patented breeding selection, 500 to 600 hours of chilling required) but more than the male parent 'T-743' (non-patented breeding selection, 300 to 400 hours of chilling required).

*Leafing.*—Plants tend to break sufficient leaf buds simultaneously with, or shortly after, anthesis.

*Canes.*—Main cane base diameter about 20 to 25 mm, color most near Grey 201C; two year old cane diameter about 10 to 15 mm, color transitioning from Greyed Orange 166B to Grey 201C; current season wood diameter about 5 to 10 mm, color Yellow Green 145C.

*Fruiting wood.*—Moderate number of twigs (about 4 to 8 common) about 15 to 20 cm in length, with internode lengths of about 20 to 25 mm common.

Foliage:

*Leaf color.*—Healthy mature leaves: top side of leaf color is Green N138B in younger leaves, transitioning to Green N137C in older leaves; under side of leaf color is Green 138C.

*Leaf arrangement.*—Alternate, simple.

*Leaf shape.*—Elliptic.

*Leaf margins.*—Nearly entire, some edges slightly crenate.

*Leaf venation.*—Pinnate with slight netting.

*Leaf apices.*—Acute.

*Leaf bases.*—Acute.

*Leaf dimensions.*—Length: about 60 to 65 mm; width: about 20 to 25 mm.

*Petioles.*—Small, about 2.5 to 3.0 mm long, about 1.5 to 2.0 mm wide; Color: Yellow Green 145C.

*Texture.*—Both upper and lower leaf surfaces glaucous; younger leaves highly glaucous.

Flowers:

*Date of* 50% anthesis.—2-year average March 6 in southeast Georgia.

*Flower shape.*—Urceolate.

*Flower bud number.*—Medium to high, averaging 3 to 6 buds per fruiting shoot.

*Flowers per cluster.*—4 to 7 common.

*Flower fragrance.*—None detected.

*Corolla color.*—White NN 155D (fully open); shades of Red-Purple 65B sometimes present prior to opening.

*Corolla length.*—About 9.5 to 10.5 mm.

*Corolla width.*—About 6.5 to 7.5 mm.

*Corolla aperture width.*—About 2.5 to 3.5 mm.

*Flower peduncle.*—Length about 8.0 to 12.0 mm; Color: Green 139D; streaks of Red-Purple 63A possible at times.

*Flower pedicel.*—Length about 5.5 to 7.5 mm; Color: Green 139D; streaks of Red-Purple 63A possible at times.

*Calyx* (*with sepals*).—Diameter: about 6.5 to 7.5 mm; Color: sepals Green 139D; calyx center Green 138D.

*Stamen.*—Length: about 6.5 to 7.0 mm; number per flower: 10; filament color: Green White 157C.

*Style.*—Length: about 9.5 to 10.5 mm; Color: Yellow Green 145B.

*Pistil.*—Length: about 12.5 to 13.5 mm; ovary color: Green 138D.

*Anther.*—Length: about 2.5 to 3.5 mm; number: 10; Color: Greyed Orange 164B to 164C.

*Pollen.*—Abundance: medium; Color: White 158B.

*Compatibility.*—The cultivar has a low degree of self-compatibility.

Fruit:

*Date of* 50% maturity.—2-year average June 1 in southeast Georgia.

*Fruit development period.*—About 87 days in southeast Georgia.

*Berry color.*—Mature fruit has a range of colors and shades, including White N 155C, Red-Purple 62 D, Greyed-Purple 186A and 186B, Greyed-Purple N186D, Greyed-Purple 185D.

*Berry flesh color.*—White 155B to White NN155B.

*Berry surface wax abundance.*—Medium.

*Berry weight.*—$1^{st}$ harvest: about 2.3 to 2.8 g; $2^{nd}$ harvest: about 1.7 to 2.2 g.

*Berry size.*—Height from calyx to scar: about 16 to 18 mm; diameter: about 16 to 18 mm.

*Berry shape.*—Nearly spherical.

*Fruit stem scar.*—Small, dry, with no tearing upon harvest.

*Calyx.*—Depth very shallow, less than about 1.0 mm; width medium, about 7.5 to 9.0 mm; sepals nearly always absent, if present, flat.

*Berry firmness.*—Very firm.

*Berry flavor and texture.*—Light sweet flavor, low acidity; texture has some slight grittiness from seeds.

*Storage quality.*—Very good.

*Suitability for mechanical harvesting.*—Likely suitable.

*Uses.*—Primarily to be used as fresh fruit for shipping and processing markets.

Seed:

*Seed abundance in fruit.*—Medium to high, with about 10 to 20 fully developed seeds per berry.

*Seed color.*—Greyed Orange N167A to Greyed Orange 164A.

*Seed dry weight.*—About 37.2 mg per 100 seed.

*Seed size.*—About 1.8 to 2.1 mm long.

It is claimed:

1. A new and distinct cultivar of the *Vaccinium* plant named 'TO-3097' as illustrated and described herein.

* * * * *